US009050295B2

(12) United States Patent
Fussenegger et al.

(10) Patent No.: US 9,050,295 B2
(45) Date of Patent: Jun. 9, 2015

(54) COMPOSITION FOR TREATMENT OF TUBERCULOSIS

(75) Inventors: Martin Fussenegger, Mägenwil (CH); Wilfried Weber, Freiburg im Breisgau (DE); Ronald Schoenmakers, Rijswijk (NL)

(73) Assignee: ETH Zurich, Zurich (CH)

( * ) Notice: Subject to any disclaimer, the term of this patent is extended or adjusted under 35 U.S.C. 154(b) by 1023 days.

(21) Appl. No.: 12/808,801

(22) PCT Filed: Nov. 25, 2008

(86) PCT No.: PCT/EP2008/066124
§ 371 (c)(1),
(2), (4) Date: Jun. 17, 2010

(87) PCT Pub. No.: WO2009/080432
PCT Pub. Date: Jul. 2, 2009

(65) Prior Publication Data

US 2011/0053880 A1 Mar. 3, 2011

(30) Foreign Application Priority Data

Dec. 21, 2007 (EP) .................................... 07024912

(51) Int. Cl.
*A61K 31/17* (2006.01)
*A61K 31/4409* (2006.01)
*A61K 45/06* (2006.01)

(52) U.S. Cl.
CPC ............. *A61K 31/17* (2013.01); *A61K 31/4409* (2013.01); *A61K 45/06* (2013.01)

(58) Field of Classification Search
None
See application file for complete search history.

(56) References Cited

U.S. PATENT DOCUMENTS 4,005,207 A 1/1977 Freerksen
6,372,752 B1 4/2002 Staveski et al.

FOREIGN PATENT DOCUMENTS

| | | | |
|---|---|---|---|
| WO | 01/56974 | | 8/2001 |
| WO | 2005/047538 | | 5/2005 |
| WO | WO2005047538 | * | 5/2005 |
| WO | 2008/003861 | | 1/2008 |

OTHER PUBLICATIONS

Frenois et al. Structure of EthR in a Ligand Bound Conformation Reveals Therapeutic Perspectives against Tuberculosis Molecular Cell, vol. 16, 301-307, Oct. 22, 2004.*

Larios et al., Synthesis of flavor and fragrance esters using *Candida antarctica* Lipase, Appl Microbiol Biotechnol (2004) 65: 373-376.*

Dörwald, F. Zaragoza. Side Reactions in Organic Synthesis: A Guide to Successful Synthesis Design, Weinheim: Wiley-VCH Verlag GmbH & Co. KGaA, 2005, Preface).*

Jordan, V. C. (Nature Reviews: Drug Discovery, 2, 2003, 205-213).*

International Search Report issued Dec. 15, 2009 in International (PCT) Application No. PCT/EP2008/066124 along with the Written Opinion.

W. Weber et al., "A Synthetic Mammalian Gene Circuit Reveals Antituberculosis Compounds", PNAS, vol. 105, No. 29, pp. 9994-9998, Jul. 22, 2008.

M. Fussenegger, "Synthetic Mammalian Gene Networks", Abstract Tutzing Symposium 2008.

F. Frenois et al., "Structure of EthR in a Ligand Bound Conformation Reveals Therapeutic Perspectives Against Tuberculosis", Molecular Cell, vol. 16, pp. 301-307, Oct. 22, 2004.

* cited by examiner

*Primary Examiner* — Jeffrey S Lundgren
*Assistant Examiner* — William Lee
(74) *Attorney, Agent, or Firm* — Wenderoth, Lind & Ponack, L.L.P.

(57) ABSTRACT

The invention relates to a pharmaceutical composition comprising a compound preventing EthR from binding to the ethA promoter, for example a compound of formula 1 wherein $R^1$ is optionally substituted phenyl or optionally substituted pyridyl; $R^2$ $(CH_2)_n$ wherein n is 1, 2, 3 or 4; $R^3$ is $CH_3(CH_2)_m$ wherein m is 0, 1, 2 or 3; $X^1$ is O, S, NH, $N(CH_3)$ or $CH_2$; and $X^2$ is O, S or NH; in particular 2-phenylethyl butyrate, and a thioamide or thiourea of formula 2 wherein $R^4$ is optionally substituted phenyl, optionally substituted pyridyl, optionally substituted indolyl, —$NR^7R^8$; or —NH—N═CH—$R^9$; and substituents $R^5$ to $R^9$ have the meanings indicated in the description, in particular ethionamide. The pharmaceutical composition is useful, e.g., in the treatment of multidrug-resistant tuberculosis.

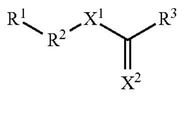

1

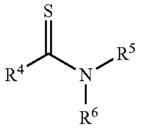

2

5 Claims, 10 Drawing Sheets

A

B
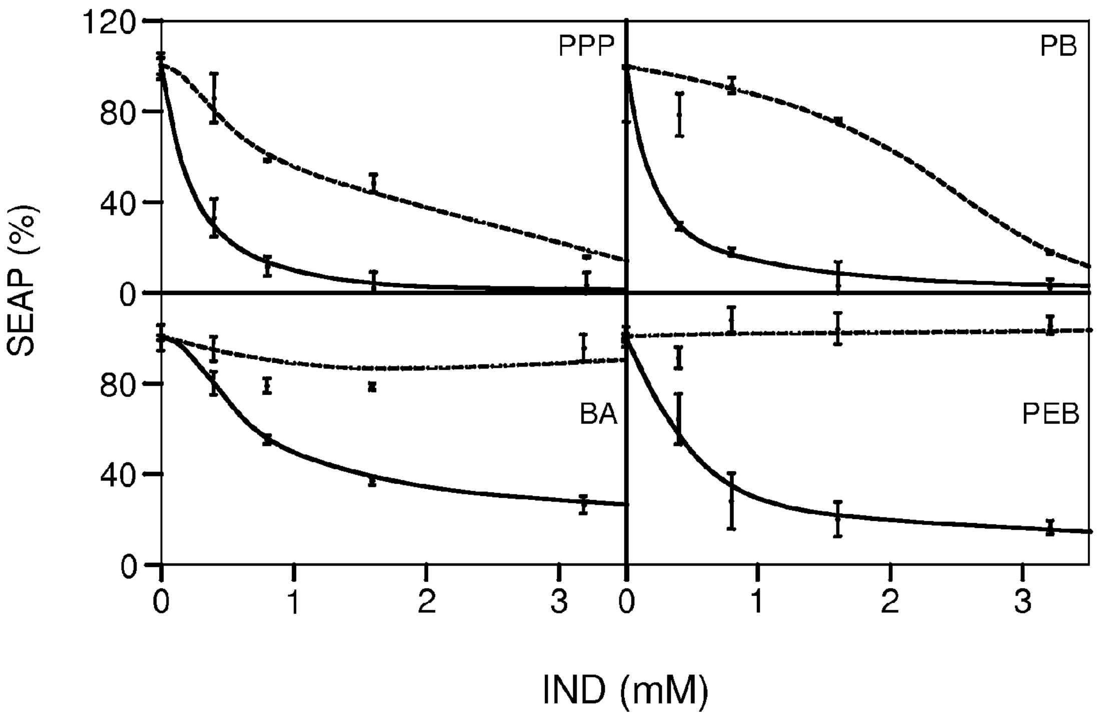
C
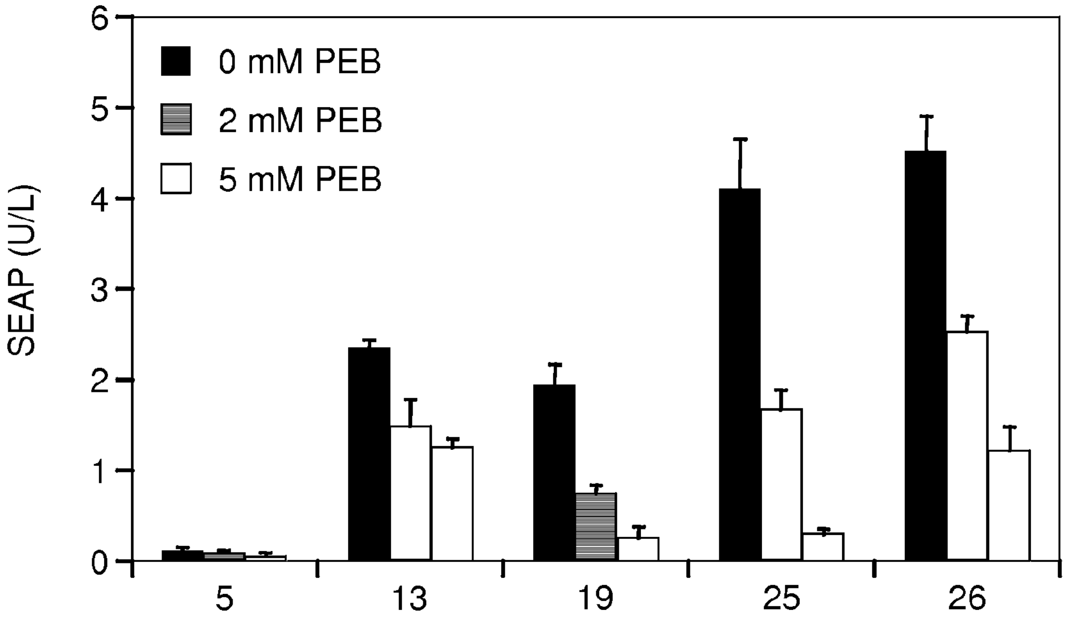

D
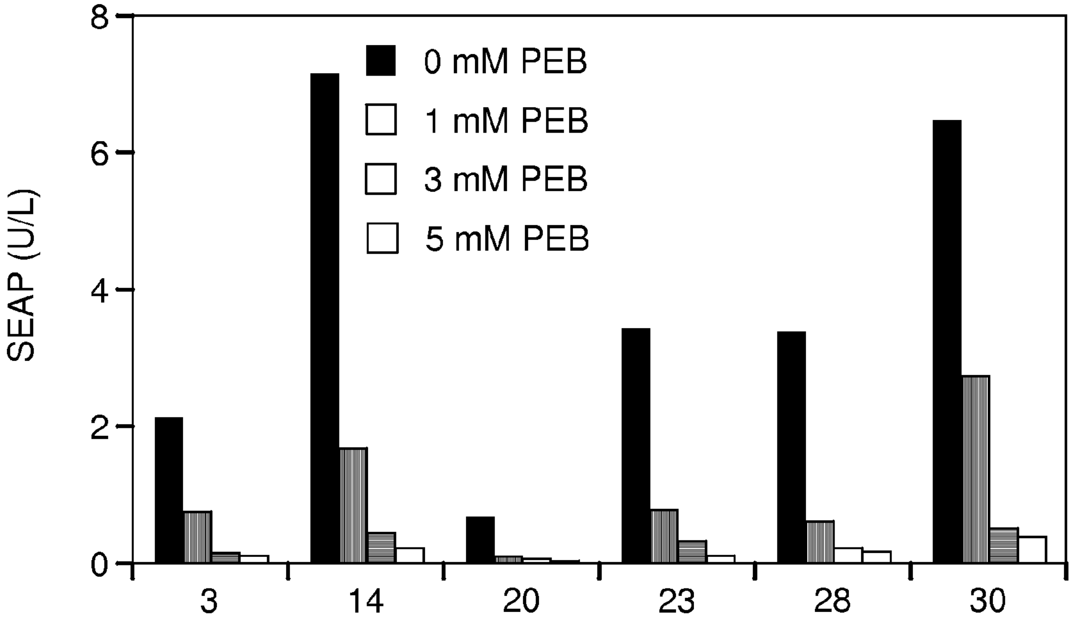
E
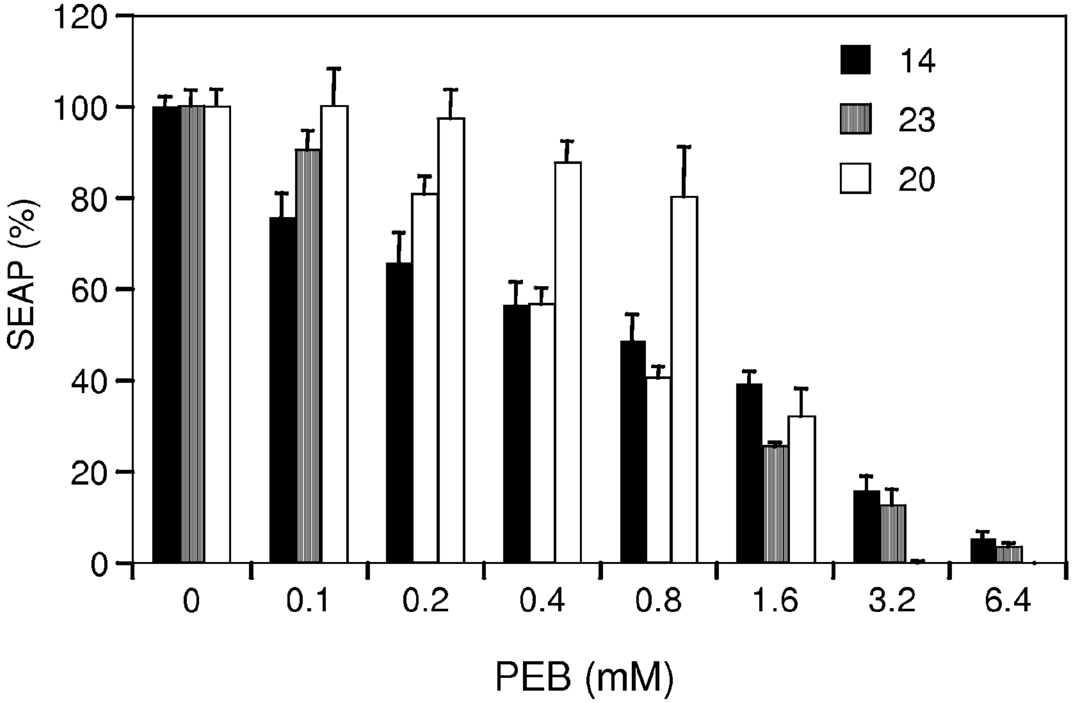

F
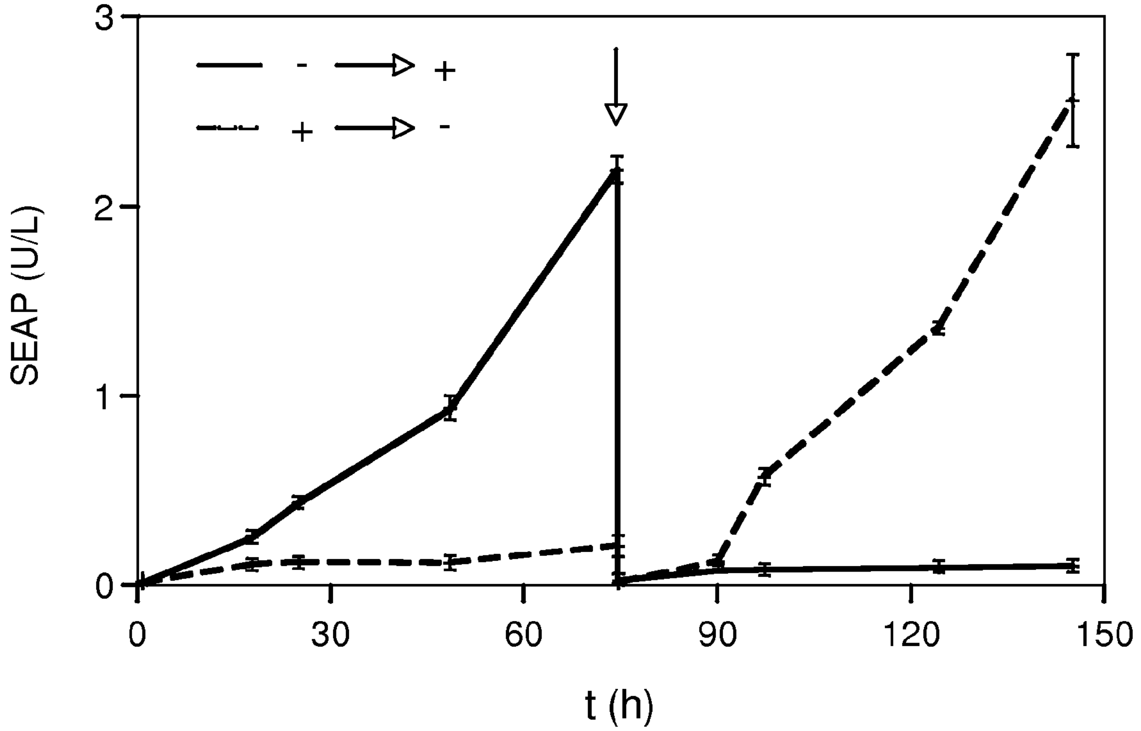

A

B
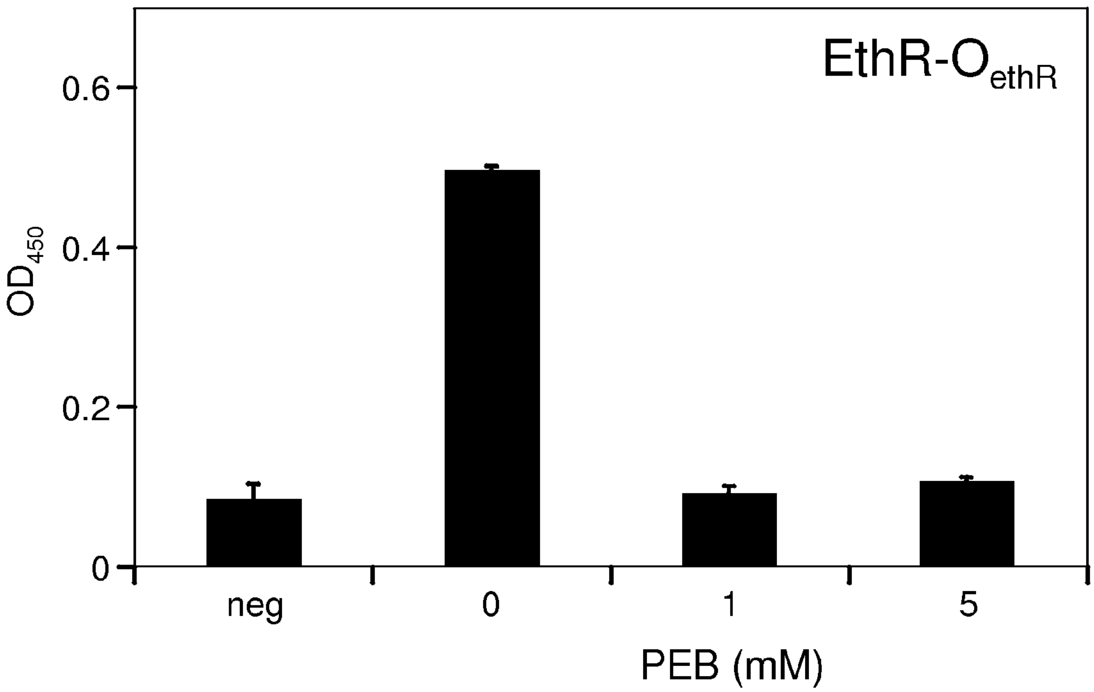
C
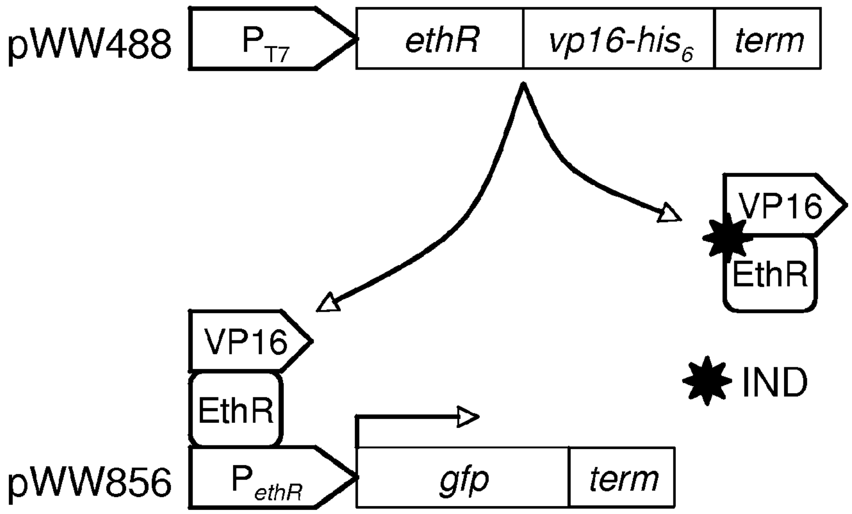

D
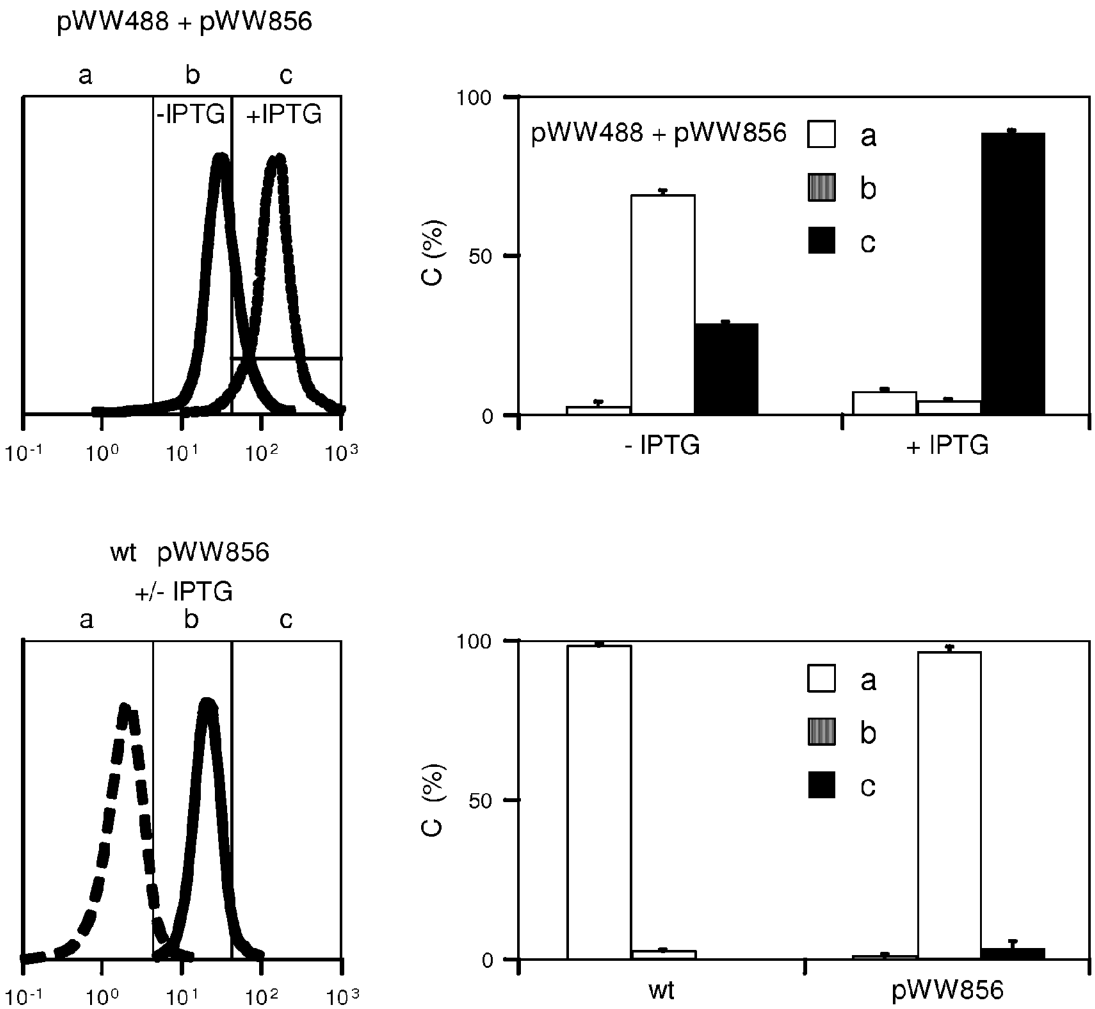

A

B
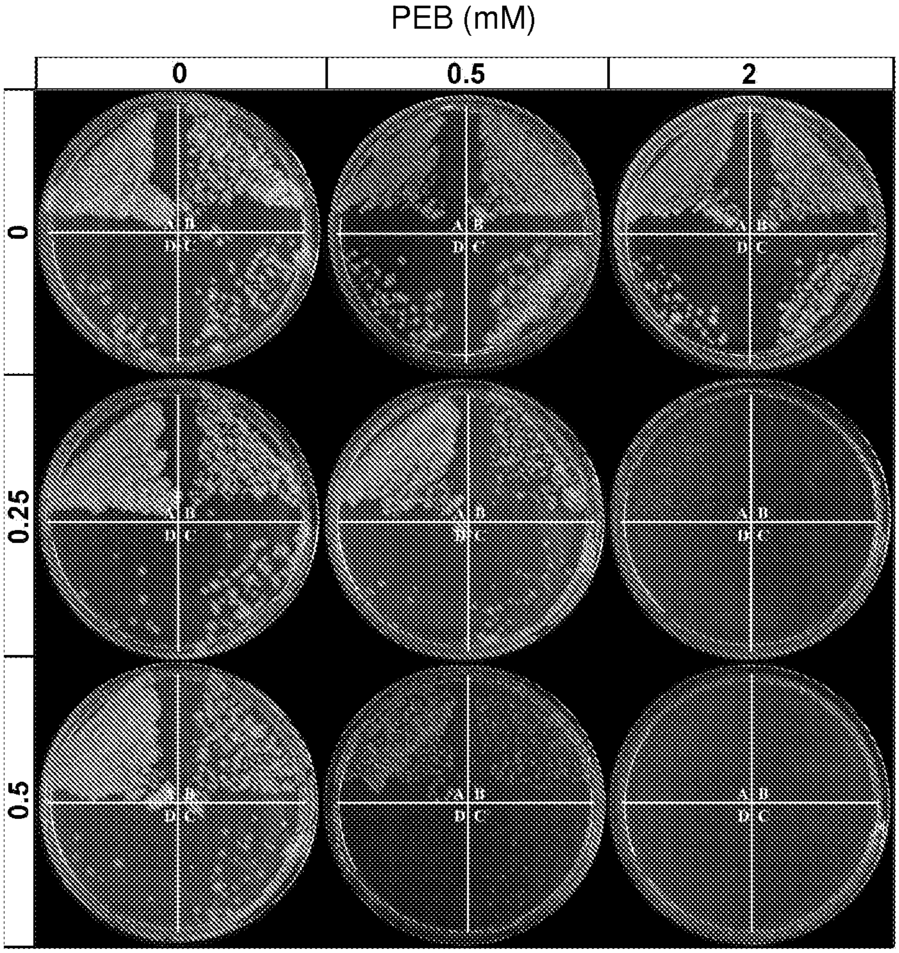
*M. tuberculosis* ŹH37Rv

SEQUENCE LISTING

```
<160> NUMBER OF SEQ ID NOS: 8

<210> SEQ ID NO 1
<211> LENGTH: 39
<212> TYPE: DNA
<213> ORGANISM: Artificial sequence
<220> FEATURE:
<223> OTHER INFORMATION: Synthetic construct; primer OWW 400

<400> SEQUENCE: 1

gcatccatat gaattccacc atgaccacct ccgcggcca                          39


<210> SEQ ID NO 2
<211> LENGTH: 44
<212> TYPE: DNA
<213> ORGANISM: Artificial sequence
<220> FEATURE:
<223> OTHER INFORMATION: Synthetic construct; primer OWW401

<400> SEQUENCE: 2

cgatcgcgcg cggctgtacg cggagcggtt ctcgccgtaa atgc                    44


<210> SEQ ID NO 3
<211> LENGTH: 76
<212> TYPE: DNA
<213> ORGANISM: Artificial sequence
<220> FEATURE:
<223> OTHER INFORMATION: Synthetic construct; O-ethR sequence

<400> SEQUENCE: 3

gacgtcgatc cacgctatca acgtaatgtc gaggccgtca acgagatgtc gacactatcg      60

acacgtagcc tgcagg                                                     76


<210> SEQ ID NO 4
<211> LENGTH: 60
<212> TYPE: DNA
<213> ORGANISM: Artificial sequence
<220> FEATURE:
<223> OTHER INFORMATION: Synthetic construct; primer OWW60
```

-continued

```
<400> SEQUENCE: 4

gctctagagc aagcttttaa tggtgatggt gatgatgccc accgtactgt caattccaag     60


<210> SEQ ID NO 5
<211> LENGTH: 43
<212> TYPE: DNA
<213> ORGANISM: Artificial sequence
<220> FEATURE:
<223> OTHER INFORMATION: Synthetic construct; primer OWW848

<400> SEQUENCE: 5

ggcttgaatt caaaggagat ataccatggt gagcaagggc gag                       43


<210> SEQ ID NO 6
<211> LENGTH: 84
<212> TYPE: DNA
<213> ORGANISM: Artificial sequence
<220> FEATURE:
<223> OTHER INFORMATION: Synthetic construct; primer OWW849

<400> SEQUENCE: 6

ggctttctag acaaaaaacc cctcaagacc cgtttagagg ccccaagggg ttatgctagt     60

tacttgtaca gctcgtccat gccg                                            84


<210> SEQ ID NO 7
<211> LENGTH: 34
<212> TYPE: DNA
<213> ORGANISM: Artificial sequence
<220> FEATURE:
<223> OTHER INFORMATION: Synthetic construct; primer OWW479

<400> SEQUENCE: 7

cgcgcatcat catcatcatc attaagcggc cgca                                 34


<210> SEQ ID NO 8
<211> LENGTH: 34
<212> TYPE: DNA
<213> ORGANISM: Artificial sequence
<220> FEATURE:
<223> OTHER INFORMATION: Synthetic construct; primer OWW480

<400> SEQUENCE: 8

agcttgcggc cgcttaatga tgatgatgat gatg                                 34
```

COMPOSITION FOR TREATMENT OF TUBERCULOSIS

This application is a U.S. national stage of International Application No. PCT/EP2008/066124 filed Nov. 25, 2008.

FIELD OF THE INVENTION

The invention relates to pharmaceutical compositions useful in the treatment of tuberculosis and related diseases.

BACKGROUND OF THE INVENTION

Up to 9 million people contract tuberculosis every year and 50 million people are presently infected with *Mycobacterium tuberculosis* resistant to both first-line drugs isoniazid and rifampicin (WHO, Fact sheet No. 104, March 2007). Ethionamide (2-ethylthioiso-nicotinamide, 2-ethylpyrimidine-4-carbothioamide), a structural analogue of isoniazid, is currently the last line of defence in the treatment of multi-drug-resistant tuberculosis (MDR-TB). During 35 years of its clinical use, ethionamide has fortunately elicited little cross-resistance with isoniazid as both prodrugs have to be activated by different mycobacterial enzymes to develop their antimicrobial activity. Yet, ethionamide continues to be prescribed at hepatotoxic doses as a consequence of EthR repressing ethA, the monooxigenase that catalyses activation of the prodrug ethionamide into an antimycobacterial nicotinamide adenine dinucleotide derivative. Up to a 1 g/day are required for an acceptable concentration in blood (Holdiness, M. R., Clin Pharmacokinet 9, 511-44 (1984)), which is associated with severe side-effects including neurotoxicity and fatal hepatotoxicity.

SUMMARY OF THE INVENTION

The invention relates to a pharmaceutical composition comprising a compound preventing EthR from binding to the ethA promoter and a thioamide or a thiourea. In particular the invention relates to such a composition comprising a compound of formula 1

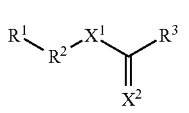

1 wherein $R^1$ is optionally substituted phenyl or optionally substituted pyridyl;

$R^2$ is $(CH_2)$, wherein n is 1, 2, 3 or 4;

$R^3$ is $CH_3(CH_2)_m$ wherein m is 0, 1, 2 or 3;

$X^1$ is O, S, NH, $N(CH_3)$ or $CH_2$; and $X^2$ is O, S or NH;

and a compound of formula 2

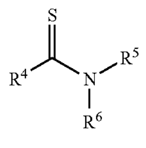

2 wherein $R^4$ is optionally substituted phenyl, optionally substituted pyridyl, optionally substituted indolyl, —$NR^7R^8$, or —NH—N═CH—$R^9$;

$R^5$ is hydrogen, $C_1$-$C_6$-alkyl, optionally substituted phenyl, optionally substituted pyridyl, or a sugar residue;

$R^6$ is hydrogen or $C_1$-$C_6$-alkyl, or $R^5$ and $R^6$ together with the N-atom to which they are bound are pyrrolidine, piperidine or morpholine;

$R^7$ is hydrogen, $C_1$-$C_6$-alkyl, optionally substituted phenyl, optionally substituted pyridyl, or a sugar residue;

$R^8$ is hydrogen or $C_1$-$C_6$-alkyl, or $R^7$ and $R^8$ together with the N-atom to which they are bound are pyrrolidine, piperidine or morpholine; and $R^9$ is optionally substituted phenyl.

Most preferred is a composition comprising a compound of formula 1 selected from 4-phenyl-2-butanone, benzyl acetate, 3-phenylpropyl propionate and 2-phenylethyl butyrate, in particular 2-phenylethyl butyrate, and a compound of formula 2 selected from ethionamide, isoxyl, N-arabinofuranosyl-N'-[ρ-(isoamyloxy)phenyl]-thiourea or thiacetazone, in particular ethionamide.

The invention likewise relates to the use of a composition comprising a compound preventing EthR from binding to the ethA promoter, e.g. 2-phenylethyl butyrate, and a thiomide or a thiourea, e.g. ethionamide, in the treatment of tuberculosis and related diseases, and to a method of treatment of tuberculosis and related diseases wherein a composition comprising a compound preventing EthR from binding to the ethA promoter and a thioamide or thiourea, e.g. ethionamide, is applied.

Furthermore the invention relates to a method of screening for compounds preventing EthR from binding to the ethA promoter useful to increase the sensitivity of multidrug-resistant *M. tuberculosis* to a thioamide or thiourea, e.g. to ethionamide.

(A) A gene fusion of ethR with the *Herpes simplex*-derived vp16 transactivation domain is expressed under the control of the simian virus 40 promoter ($P_{SV40}$, plasmid pWW489) in HEK-293. The chimeric transactivator EthR-VP16 binds to its operator $O_{ethR}$ thereby activating transcription from the minimal *Drosophila* heat shock 70 promoter ($P_{hsp70min}$), driving expression of human placental secreted alkaline phosphatase (seap, plasmid pWW491). In the presence of a cell-permeable, non-cytotoxic inducer (IND), binding of EthR-VP16 to the promoter is inhibited, thereby resulting in transcriptional silence (broken lines). Non cell-permeable or cytotoxic compounds are automatically excluded from the hit list.

(B) Screening of a rationally designed compound library using the EthR-based gene network. 30,000 HEK-293 cells containing either the EthR-based gene network (pWW489 and pWW491, results shown with solid line) or an isogenic constitutive SEAP expression network (pWW35 and pWW37, results shown with dotted line) are cultivated for 48 h in the presence of potential inducers (IND) prior to SEAP profiling. SEAP expression was normalized to 100%.

x-axis: concentration of test substance (mM);

y-axis: SEAP production (%); PPP, 3-phenylpropyl propionate; PB, 4-phenyl-2-butanone; BA, benzyl acetate; PEB, 2-phenylethyl butyrate.

(C) Clonal variability of HEK cells stably transduced with a retroviral vector encoding ethR-vp16 (pWW871, $_{EthR}$HEK). Individual clones (40,000 cells) are further transfected with plasmid pWW491 (see FIG. 1A) and cultivated at the indicated 2-phenlyethyl butyrate (PEB) concentrations for 48 h prior to quantifying SEAP production.

x-axis: clone identification number.

(D) Clonal variability of HEK cells double transgenic for pWW871 and pWW491 ($_{EthR}$HEK-SEAP). 40,000 $_{EthR}$HEK-SEAP cells are cultivated at the indicated 2-phenlyethyl butyrate (PEB) concentrations for 48 h prior to quantifying SEAP production.

x-axis: clone identification number.

(E) Dose-response characteristics of the synthetic gene switch. 40,000 double transgenic $_{EthR}$HEK-SEAP cells are cultivated at increasing 2-phenylethyl butyrate (PEB) concentrations for 48 h prior to quantifying SEAP production. The different bars for each concentration represent the different clones tested (clone identification numbers 14, 23, 20).

(F) Reversibility of the synthetic gene circuit. 200,000 $_{EthR}$HEK-SEAP cells are alternately cultivated in the absence (−) or presence (+) of 3.2 mM 2-phenlyethyl butyrate and SEAP production is profiled at indicated time points. At 72 h, the inducer status is reversed (arrow).

x-axis: time (t)

Figure 2:
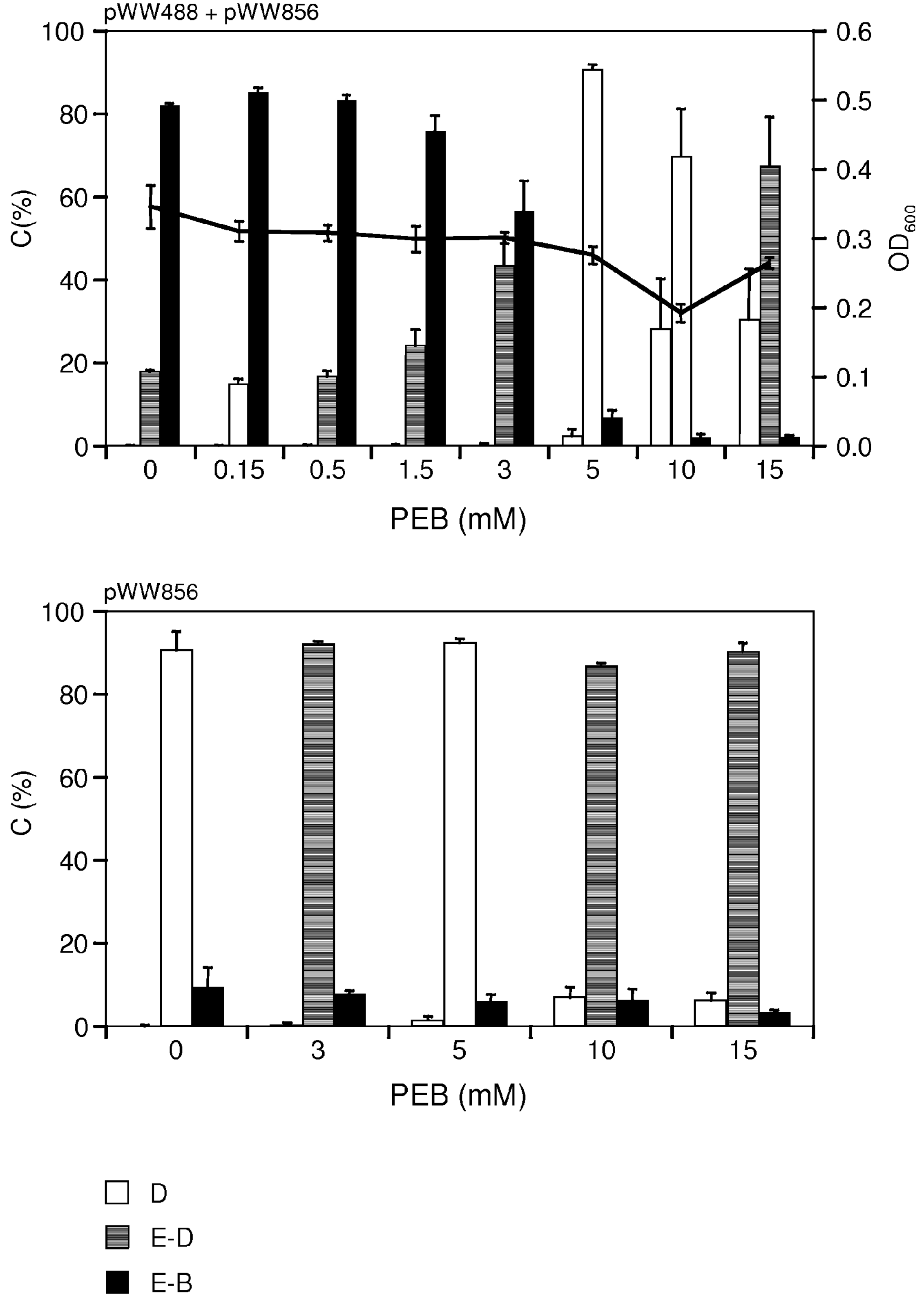

FIG. 2. Validation of the inducer in bacteria and in a cell-free system (A) Effect of 2-phenylethyl butyrate in *E. coli.*

Upper panel: *E. coli* BL21(DE3), transformed with pWW488 and pWW856 (see FIG. 2C), is grown in the presence of IPTG at the indicated 2-phenylethyl butyrate (PEB) concentrations for 5.5 h prior to analyzing the cells by FACS. The optical density at 600 nm ($OD_{600}$) after the growth period is indicated as well.

Lower panel: As a control, *E. coli* BL21(DE3) transformed with pWW856 alone are used in parallel.

y-axis: percentage of gates cells. Gates: D, dead cells; E-D, cells with EthR dissociated from operator, EthR not present; E-B, cells with EthR bound to operator.

(B) Impact of 2-phenylethyl butyrate on the interaction between EthR and $O_{ethR}$ in vitro. Biotinylated operator $O_{ethR}$ immobilized on streptavidin-agarose beads is incubated in the presence or absence of 2-phenylethyl butyrate (PEB) at the indicated concentrations in a cell lysate of *E. coli* BL21 (DE3) transformed with pWW862 ($P_{T7}$-ethR-$his_6$-term) for production of hexahistidine($his_6$)-tagged EthR. Following washing, $his_6$-tagged EthR is detected by a monoclonal anti-$his_6$ antibody coupled to horseradish peroxidase, resulting in the conversion of 3,3',5,5'-tetramethylbenzidine to a colored formazane which is subsequently quantified via its absorption at 450 nm ($OD_{450}$). As negative controls, non-recombinant cell lysate is used (neg).

(C) Genetic setup of the screening system in bacteria. ethR-vp16 is expressed under the control of the phage T7 promoter ($P_{T7}$, plasmid pWW488). In the absence of the inducer, EthR-VP16 activates the chimeric promoter $P_{ethR}$ and induces transcription of gfp (plasmid pWW856). In the presence of the inducer (IND), EthR-VP16 binding is inhibited, resulting in transcriptional silence.

(D) Characterization of the screening system. *E. coli* BL21 (DE3), transformed with pWW488 and pWW856, are grown in the presence or absence of IPTG for 5.5 h prior to FACS analysis. As controls, wild-type (wt) bacteria or bacteria transformed with pWW856 alone are used. The cell populations are grouped into three categories according to their fluorescence levels (gates a, b, c).

Figure 3:
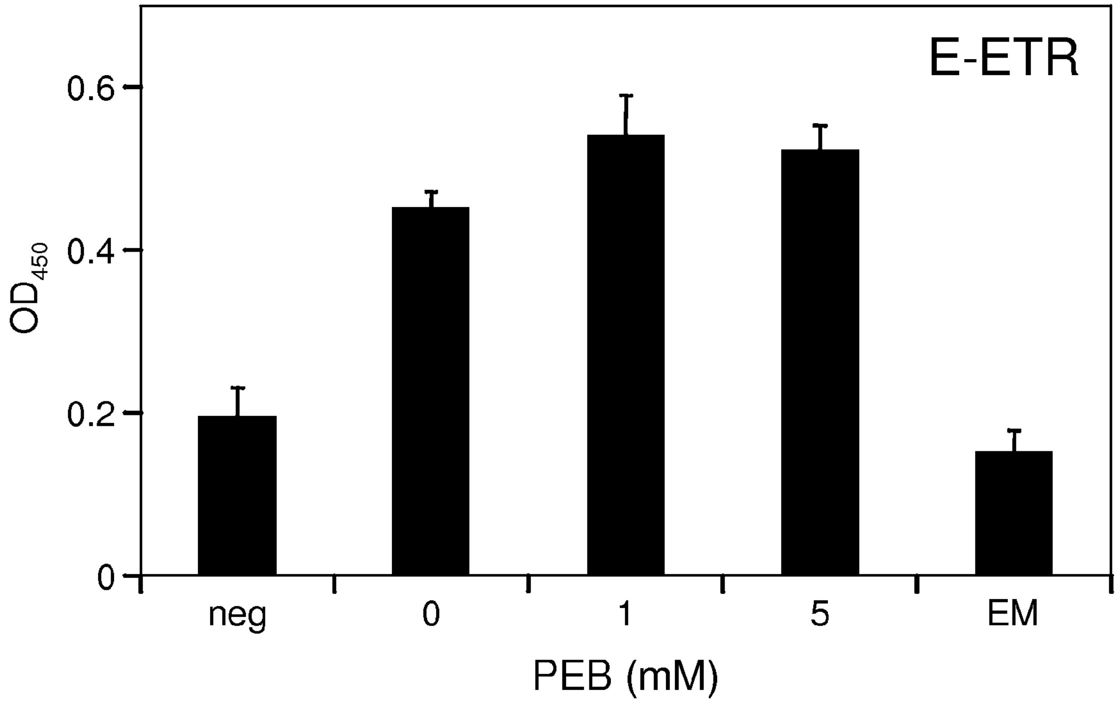

FIG. 3. Specificity of the 2-phenylethyl butyrate activity.

To exclude that 2-phenylethyl butyrate indiscriminatingly modulates protein-DNA interactions the macrolide-dependent repressor-operator configuration is challenged with this compound in an identical ELISA set-up as shown in FIG. 2B. The E-ETR interaction is insensitive to 2-phenylethyl butyrate (PEB) and can exclusively be abolished in the presence of erythromycin (EM, 5 μg/ml).

Figure 4:
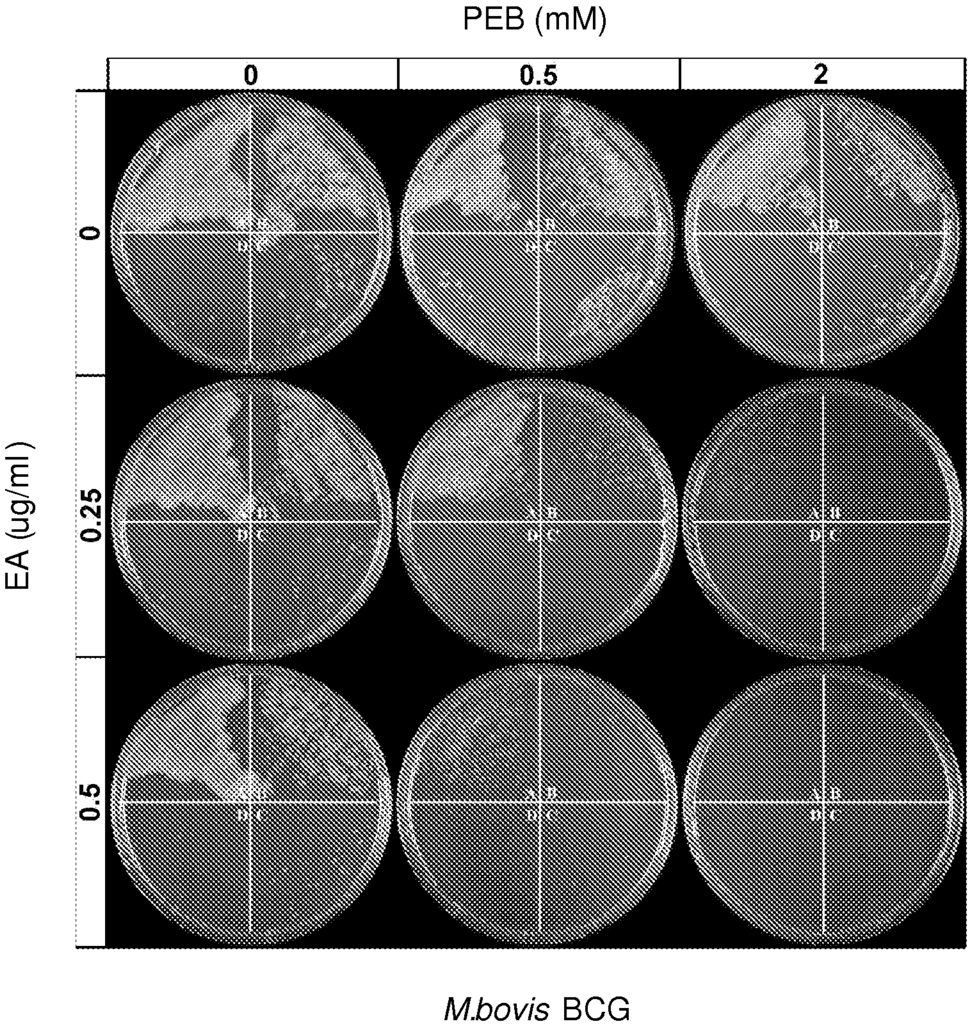

FIG. 4. Effect of 2-phenylethyl butyrate and ethionamide on *M. bovis* BCG and *M. tuberculosis.*

(A) Synergistic effect of 2-phenylethyl butyrate (PEB) and ethionamide (EA) on the growth inhibition of *M. bovis* BCG. A, B, C and D correspond to serial dilutions ($10^{-2}$, $10^{-3}$, $10^{-4}$ and $10^{-5}$) of an *M. bovis* BCG settling culture ($OD_{600}$: 0.6).

(B) Synergistic effect of 2-phenylethyl butyrate (PEB) and ethionamide (EA) on growth inhibition of *M. tuberculosis* H37Rv. A, B, C and D correspond to serial dilutions ($10^{-2}$, $10^{-3}$, $10^{-4}$ and $10^{-5}$) of an *M. tuberculosis* H37Rv settling culture ($OD_{600}$: 0.4).

DETAILED DESCRIPTION OF THE INVENTION

The invention relates to a pharmaceutical composition comprising a compound preventing EthR from binding to the ethA promoter and a thioamide or thiourea.

Preferably, the compound preventing EthR from binding to the ethA promoter is a compound of formula 1

1

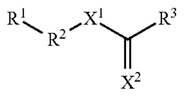

wherein $R^1$ is optionally substituted phenyl or optionally substituted pyridyl;

$R^2$ is $(CH_2)$, wherein n is 1, 2, 3 or 4;

$R^3$ is $CH_3(CH_2)_m$ wherein m is 0, 1, 2 or 3;

$X^1$ is O, S, NH, $N(CH_3)$ or $CH_2$; and $X^2$ is O, S or NH.

The pharmaceutical composition of the invention further comprises a thioamide or thiourea, which is preferably a compound of formula 2

2

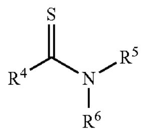

wherein $R^4$ is optionally substituted phenyl, optionally substituted pyridyl, optionally substituted indolyl, —$NR^7R^8$; or —NH—N═CH—$R^9$;

$R^5$ is hydrogen, $C_1$-$C_6$-alkyl, optionally substituted phenyl, optionally substituted pyridyl, or a sugar residue;

$R^6$ is hydrogen or $C_1$-$C_6$-alkyl, or $R^5$ and $R^6$ together with the N-atom to which they are bound are pyrrolidine, piperidine or morpholine;

$R^7$ is hydrogen, $C_1$-$C_6$-alkyl, optionally substituted phenyl, optionally substituted pyridyl, or a sugar residue;

$R^8$ is hydrogen or $C_1$-$C_6$-alkyl, or $R^7$ and $R^8$ together with the N-atom to which they are bound are pyrrolidine, piperidine or morpholine; and $R^9$ is optionally substituted phenyl.

Alkyl is in particular $C_1$-$C_6$-alkyl, for example $C_1$-$C_4$-alkyl, $C_1$-$C_4$-Alkyl is methyl, ethyl, propyl, e.g. n-propyl or iso-propyl, or butyl, e.g. n-butyl, iso-butyl or tert-butyl, $C_1$-$C_6$-Alkyl is methyl, ethyl, propyl or butyl as described, or also pentyl, e.g. n-pentyl or iso-pentyl, or hexyl, e.g. n-hexyl or iso-hexyl.

Optionally substituted phenyl is unsubstituted phenyl or phenyl substituted by one, two or three substituents selected from $C_1$-$C_6$-alkyl, e.g. methyl, trifluoromethyl, $C_1$-$C_6$-alkoxy, e.g. methoxy, ethoxy or iso-pentoxy, $C_1$-$C_6$-alkylcarbonyl, e.g. acetyl, $C_1$-$C_6$-alkyl-carbonyloxy, e.g. acetoxy, $C_1$-$C_6$-alkylthio, e.g. methylthio, nitro, amino, $C_1$-$C_6$-alkylamino, e.g. methylamino or ethylamino, di-$C_1$-$C_6$-alkylamino, e.g. dimethylamino or diethylamino, pyrrolidino, piperidino, morpholino, $C_1$-$C_6$-alkylcarbonylamino, e.g. acetylamino, and halogen. Halogen is fluoro, chloro, bromo or iodo, particularly fluoro or chloro. Preferably optionally substituted phenyl is phenyl or phenyl substituted by one or two of the mentioned substituents, in particular one of the mentioned substituents in ortho, meta or para position, preferably in meta or para position. For example, optionally substituted phenyl is phenyl, methyl- or dimethylphenyl, trifluoromethylphenyl, methoxyphenyl, ethoxyphenyl, acetoxyphenyl, nitrophenyl, dinitrophenyl, aminophenyl, methylamino-phenyl, dimethylaminophenyl, fluorophenyl, chlorophenyl or dichlorophenyl.

Optionally substituted pyridyl is 2-, 3- or 4-pyridyl, unsubstituted or substituted by one or two substituents selected from $C_1$-$C_6$-alkyl, e.g. methyl or ethyl, trifluoromethyl, $C_1$-$C_6$-alkoxy, e.g. methoxy or ethoxy, nitro, amino, $C_1$-$C_6$-alkylamino, e.g. methylamino or ethylamino, di-$C_1$-$C_6$-alkylamino, e.g. dimethylamino or diethylamino, $C_1$-$C_6$-alkylcarbonylamino, e.g. acetylamino, and halogen. Halogen is fluoro, chloro, bromo or iodo, particularly fluoro or chloro.

Optionally substituted indolyl is 1H-2-, 3-, 4-, 5-, 6-, or 7-indolyl, unsubstituted or substituted by one or two substituents selected from $C_1$-$C_6$-alkyl, e.g. methyl or ethyl, trifluoromethyl, $C_1$-$C_6$-alkoxy, e.g. methoxy or ethoxy, nitro, amino, $C_1$-$C_6$-alkylamino, e.g. methylamino or ethylamino, di-$C_1$-$C_6$-alkylamino, e.g. dimethylamino or diethylamino, $C_1$-$C_6$-alkylcarbonylamino, e.g. acetylamino, and halogen.

A sugar residue is

L- or D-furanosyl selected from the aldopentoses arabinose, lyxose, ribose and xylose of formula 3;

L- or D-hexofuranosyl selected from the aldohexoses allose, altrose, glucose, mannose, gulose, idose, galactose and talose of formula 4;

L- or D-hexofuranosyl selected from the ketohexoses fructose, psicose, sorbose and tagatose of formula 5;

L- or D-pyranosyl selected from the aldohexoses allose, altrose, glucose, mannose, gulose, idose, galctose and talose of formula 6; or L- or D-pyranosyl selected from the ketohexoses fructose, psicose, sorbose and tagatose of formula 7;

3

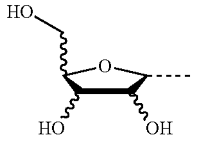

4

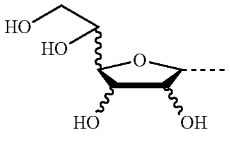

-continued

5

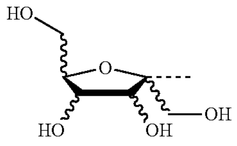

6

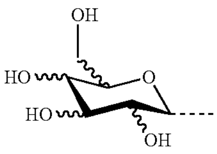

7

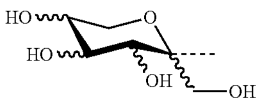

in which one, two, three or four hydroxy groups can be methylated, benzylated or acetylated, or one hydroxy group can be replaced by hydrogen, halogen, methylamino, ethylamino, or acetamido.

Particularly preferred in the compound of formula 1 is $R^1$ with the meaning phenyl. Also particularly preferred in the compound of formula 1 is $X^1$ with the meaning O or $CH_2$ and $X^2$ with the meaning O, i.e. an ester or a ketone.

Most preferred is compound of formula 1 selected from 4-phenyl-2-butanone, benzyl acetate, 3-phenylpropyl propionate and 2-phenylethyl butyrate, in particular 2-phenylethyl butyrate.

Preferred compounds of formula 2 are those wherein $R^4$ is optionally substituted pyridyl, $NR^7R^8$, or —NH—N=CH—$R^9$;

$R^5$ is hydrogen, optionally substituted phenyl, or a sugar residue;

$R^6$ is hydrogen;

$R^7$ is optionally substituted phenyl or a sugar residue;

$R^8$ is hydrogen; and $R^9$ is optionally substituted phenyl.

Even more preferred are compounds of formula 2 wherein $R^4$ is substituted pyridyl, $NR^7R^8$, or —NH—N=CH—$R^9$;

$R^5$ is hydrogen, substituted phenyl, or a sugar residue;

$R^6$ is hydrogen;

$R^7$ is substituted phenyl or a sugar residue;

$R^8$ is hydrogen; and $R^9$ is substituted phenyl.

Most preferred are compounds of formula 2 wherein $R^4$ is pyridyl substituted by $C_1$-$C_6$-alkyl, $NR^7R^8$, or —NH—N=CH—$R^9$;

$R^5$ is hydrogen, phenyl substituted by $C_1$-$C_6$-alkoxy, or a sugar residue;

$R^6$ is hydrogen;

$R^7$ is phenyl substituted by $C_1$-$C_6$-alkoxy, or a sugar residue;

$R^8$ is hydrogen; and $R^9$ is phenyl substituted by $C_1$-$C_6$-alkylcarbonylamino.

Particularly preferred compounds are compounds of formula 2 wherein $R^4$ is 4-pyridyl substituted by $C_1$-$C_6$-alkyl; $R^5$ is hydrogen or a sugar residue; and $R^6$ is hydrogen; in particular ethionamide of formula 8:

8

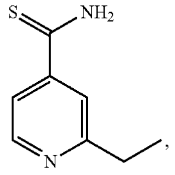

compounds of formula 2 wherein $R^4$ is —NH—N═CH—$R^9$; $R^5$ is hydrogen or a sugar residue; $R^6$ is hydrogen; and $R^9$ is phenyl substituted by $C_1$-$C_6$-alkylcarbonylamino, in particular thiacetazone of formula 9:

9

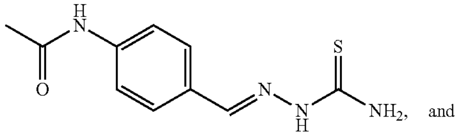

and compounds of formula 2 wherein $R^4$ is —$NR^7R^8$; $R^5$ is phenyl substituted by $C_1$-$C_6$-alkoxy; $R^6$ is hydrogen; $R^7$ is phenyl substituted by $C_1$-$C_6$-alkoxy or a sugar residue; and $R^8$ is hydrogen; in particular isoxyl of formula 10:

10

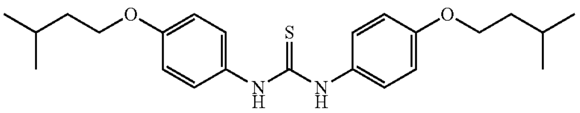

or the isoxyl analog N-arabinofuranosyl-N'-[ρ-(isoamyloxy)phenyl]-thiourea of formula 11:

11

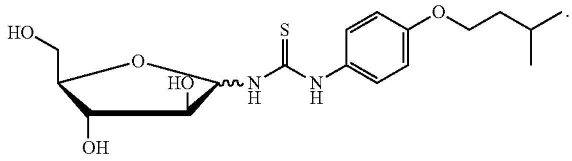

Compounds of formula 1 are known are can be made according to methods well known in the art.

Compounds of formula 2 are known or can be manufactured as follows:

Thioamides, i.e. compounds of formula 2 wherein $R^4$ is optionally substituted phenyl, optionally substituted pyridyl or optionally substituted indolyl, are obtainable by reacting an amine of formula $HNR^5R^6$ with a carboxylic acid of formula $R^4$—COON to form an amide of formula $R^4$—CO—$NR^5R^6$. The amide is reacted with Lawesson's reagent or phosphorus pentasulfide, to obtain the thioamide of formula 2. Another method to synthesize the thioamides is via the Kindler modification of the Willgerodt reaction using an aldehyde of formula $R^4$—CH═O and an amine of formula $HNR^5R^6$ and react them in the presence of sulphur.

Thioureas, i.e. compounds of formula 2 wherein $R^4$ is —$NR^7R^8$, are obtainable by reacting a bromide with potassium thiocyanate to give an isothiocyanate of formula $R^5$—N═C═S or $R^7$—N═C═S, which is reacted with an amine of formula $HNR^7R^8$ or $HNR^5R^6$, respectively. Corresponding hydrazones, i.e. compounds of formula 2 wherein $R^4$ is —NH—N═CH—$R^9$, are obtainable by reacting an aldehyde of formula $R^9$—CH═O with an hydrazinocarbothioamide of formula $R^5R^6$N—(C═S)—NH—$NH_2$.

Furthermore the invention relates to a method of screening for compounds preventing EthR from binding to the ethA promoter. An EthR-based synthetic mammalian gene circuit allows to determine, whether a compound could be used together with ethionamide in the treatment of tuberculosis.

For the purpose of the invention, EthR is a polypeptide derived from *M. tuberculosis* EthR [Dover, L. G. et al., J Mol Biol 340, 1095-105 (2004)]. By "derived from" is meant, in this context, that the polypeptide comprises protein domains that contain amino acid substitutions, preferably conservative amino acid substitutions, but remain at least 70%, preferably 80%, and more preferably 90% or more identical to the naturally occurring *M. tuberculosis* EthR at the amino acid level.

"Conservative substitution" is known in the art and is described e.g. by Dayhof, M. D., 1978, Nat. Biomed. Res. Found., Washington, D.C., Vol. 5, Sup. 3. Genetically encoded amino acids are generally divided into four groups: (1) acidic=aspartate and glutamate; (2) basic=lysine, arginine, and histidine; (3) non-polar=alanine, valine, leucine, isoleucine, proline, phenylalanine, methionine, and tryptophan; and (4) uncharged polar=glycine, asparagine, glutamine, cysteine, serine, threonine, and tyrosine. Phenylalanine, tryptophan and tyrosine are also jointly classified as aromatic amino acids. A substitution in a protein of one amino acid classified in a particular group by another amino acid in the same group is generally regarded as a conservative substitution.

For the purpose of the invention, $O_{ethR}$ is a polynucleotide related to the *M. tuberculosis* ethA promoter, which is defined in Engohang-Ndong, J. et al., Mol Microbiol 51, 175-88 (2004). By an $O_{ethR}$ sequence "related to" the *M. tuberculosis* ethA promoter is meant, in this context, that the polynucleotide sequence of $O_{ethR}$ contains base changes or modified nucleotides compared to the naturally occurring polynucleotide, but still can bind the EthR either constitutively or in a small molecule-dependent way.

Figure 1:
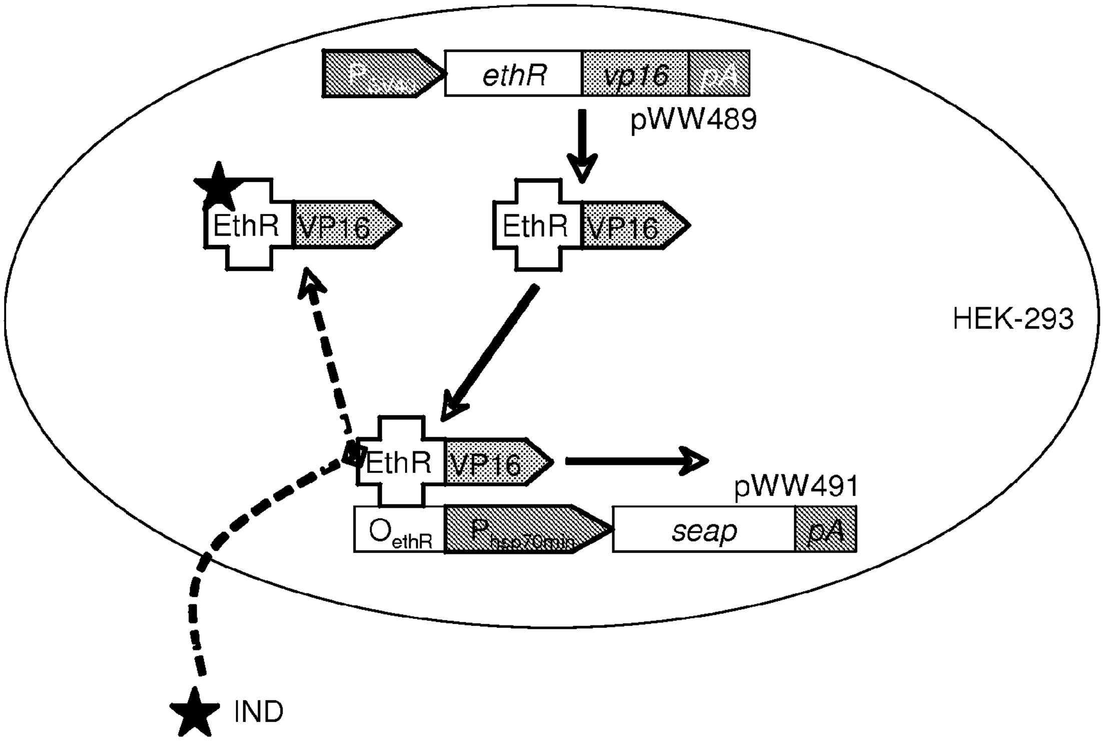
FIG. 1. EthR-based synthetic gene network in mammalian cells.

Structural analysis classifying EthR as a TetR/CamR family repressor suggests the existence of compounds that could modulate the affinity of EthR for its $O_{ethR}$ operator [Dover, L. G. et al., J Mol Biol 340, 1095-105 (2004)]. Following a synthetic biology approach a gene network whose topology enables detection of EthR-binding molecules inside human cells is designed, thereby scoring for non-cytotoxic and bioavailable compounds accessing the pathogenic habitat of *M. tuberculosis* (FIG. 1A). The gene circuit consists of a synthetic transactivator, EthR fused to the VP16 transactivation domain of *Herpes simplex* (pWW489, $P_{sv40}$-EthR-VP16-pA), which induces SEAP (human placental secreted alkaline phosphatase) expression in human embryonic kidney cells (HEK-293) after binding to a chimeric promoter containing $O_{ethR}$ 5' of a minimal *Drosophila* heat shock protein 70 promoter ($P_{hsp90min}$; pWW491, $O_{ethR}$-$P_{hsp70min}$-SEAP-pA, 8.2±0.8 U/L; background level of pWW491 0.4±0.1 U/L, FIG. 1*a*). Cell-permeable EthR-interacting compounds are expected to release EthR-VP16 from $O_{ethR}$-$P_{hsp70min}$, thereby repressing SEAP production to basal levels (FIG. 1A). Interestingly, hexadecyl octanoate (10 mM; ClogP=11.29), identified in cristallography studies to compromise EthR's DNA-binding capacity [Frenois, F. et al., Mol Cell 16, 301-7, 2004], fails to decrease SEAP expression in HEK-293 containing pWW489 and pWW491, suggesting that it remains a non-trivial challenge to develop bioavailable EthR-binding compounds.

In more general terms, the invention relates to a method of screening for compounds preventing EthR from binding to the $O_{ethR}$ operator. In particular, the $O_{ethR}$ operator or a derivative thereof is functionally linked to a mammalian cell-compatible promoter in a way, that binding of EthR to $O_{ethR}$ modulates the transcriptional activity of said mammalian cell-compatible promoter. The transcriptional activity of said mammalian cell-compatible promoter can be analyzed by placing a suitable reporter gene (e.g. human placental secreted alkaline phosphatase (SEAP), a fluorescent protein or a luciferase) under the control of said promoter. In order to enhance the transcriptional activity-modulating effect of EthR, it can optionally be functionally linked to a transactivator or transrepressor domain (a non-limiting selection of which are cited in U.S. Pat. No. 6,287,813). The screening is performed by contacting a test compound with a mammalian cell harbouring said mammalian cell-compatible promoter functionally linked to $O_{ethR}$ and a suitable reporter gene and further harbouring EthR optionally fused to a transactivator or transrepressor domain. A change in reporter gene expression indicates that the test compound might interfere with binding of EthR to its operator $O_{ethR}$.

In the method of screening for compounds preventing EthR from binding to the ethA promoter of the invention, compounds are tested in mammalian cells comprising the $O_{ethR}$ operator or a derivative thereof functionally linked to a mammalian cell-compatible promoter in a way, that binding of EthR to $O_{ethR}$ modulates the transcriptional activity of said mammalian cell-compatible promoter, and the test compound is determined to be a compound preventing EthR from binding to the ethA promoter if it represses expression of a reporter gene under control of said mammalian cell-compatible promoter.

Capitalizing on cristallography data [Dover, L. G. et al., J Mol Biol 340, 1095-105 (2004)] describing EthR's small-molecule binding site as "hydrophobic tunnel-like cavity fitting a lipophilic ligand" and on the observation that repressors are often feed-back controlled by the substrates or products of their target gene, a library of hydrophilic ketones and esters with ClogP values below 4 to enable screening in aqueous solutions (Table 1) is analyzed.

TABLE 1

| Compound | Structure | Formula | $M_w$ | ClogP |
|---|---|---|---|---|
| Methyl hexanoate | 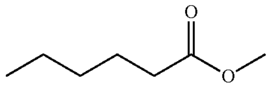 | $C_7H_{14}O_2$ | 130.18 | 2.298 |
| Butyl propionate | 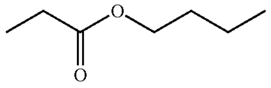 | $C_7H_{14}O_2$ | 130.18 | 2.298 |
| Pentyl acetate | 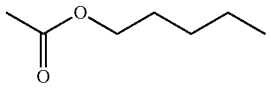 | $C_7H_{14}O_2$ | 130.18 | 2.298 |
| 4-Phenyl-2-butanone | 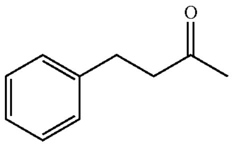 | $C_{10}H_{12}O$ | 148.20 | 1.889 |
| Methyl phenylacetate | 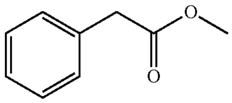 | $C_9H_{10}O_2$ | 150.17 | 1.820 |
| Benzyl acetate | 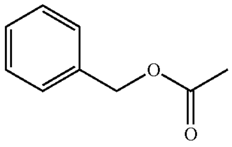 | $C_9H_{10}O_2$ | 150.17 | 1.960 |
| 2-Phenylethyl acetate | 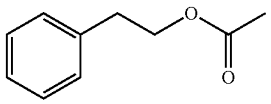 | $C_{10}H_{12}O_2$ | 164.20 | 2.279 |
| 2-Phenylethyl propionate | 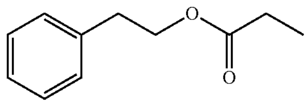 | $C_{11}H_{14}O_2$ | 178.23 | 2.808 |

TABLE 1-continued

| Compound | Structure | Formula | $M_w$ | ClogP |
| --- | --- | --- | --- | --- |
| 2-Phenylethyl butyrate | 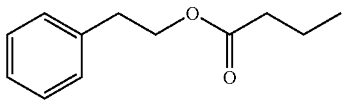 | $C_{12}H_{16}O_2$ | 192.25 | 3.337 |
| 3-Phenylpropyl propionate | 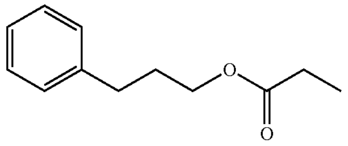 | $C_{12}H_{16}O_2$ | 192.25 | 3.187 |
| 2-Phenylethyl isopentanoate | 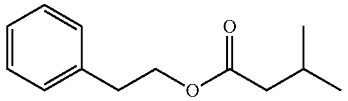 | $C_{13}H_{18}O_2$ | 206.28 | 3.736 |
| Hexadecyl octanoate | 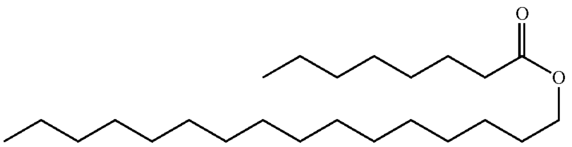 [SMILES: CCCCCCCCCCCCCCCCOC(=O)CCCCCCC] | $C_{24}H_{48}O_2$ | 368.64 | 11.29 |

When HEK-293 populations containing the EthR-based gene circuit are exposed to 0-3.2 mM of individual library components, only 4-phenyl-2-butanone, benzyl acetate, 3-phenylpropyl propionate and 2-phenylethyl butyrate induce a significant decrease in SEAP expression. As the SEAP production decline does not correlate with cytotoxicity (assessed by using HEK-293 engineered for isogenic constitutive SEAP expression) these compounds may release EthR-VP16 from $O_{etR}$-$P_{hsp90min}$ (FIG. 1B).

2-Phenylethyl butyrate ($IC_{50}$=0.5 mM) is preferred, since it does not show cytotoxity and demonstrates reasonable activity (FIG. 1B). Furthermore, 2-phenylethyl butyrate is a licensed food additive, see Joint FAO/WHO Expert Committee on Food Additives, JECFA No. 991.

2-Phenylethyl butyrate retains its regulating activity in vivo. Microencapsulated $_{EthR}$HEK-SEAP (transgenic for pWW489 and pWW491; see FIGS. 1C and 1D for clonal variation, FIG. 1E for adjustability and FIG. 1F for reversibility of the gene circuit) is implanted intraperitoneally into mice which are subsequently injected with 2-phenylethyl butyrate (625 μl/kg). 2-Phenylethyl butyrate significantly reduces SEAP serum levels of treated mice (with 2-phenylethyl butyrate 0.21±0.03 U/L; without 2-phenylethyl butyrate: 0.42±0.04 U/L)) suggesting that this compound is bioavailable and reaching EthR-inactivating concentrations inside target cells.

*Escherichia coli*, engineered for EthR-controlled GFP expression shows adjustable green fluorescence when exposed to 2-phenylethyl butyrate levels previously used in vivo, indicating that this compound also triggers release of EthR from $O_{ethR}$ in prokaryotes (FIGS. 2A, 2C and 2D showing FACS parameters). Indeed, when using an ELISA combining immobilized $O_{ethR}$ with $His_6$-tagged EthR (FIG. 2B) (or $E^{17}$ and ETR as specificity control, FIG. 3) produced in *E. coli* it is confirmed that 2-phenylethyl butyrate exclusively and specifically modulates the EthR-$O_{ethR}$ interaction.

The repressor protein E binds to its cognate operator sequence ETR and is released thereof in the presence of macrolide antibiotics like erythromycin as described in U.S. Pat. No. 7,273,723.

Growth of *M. tuberculosis* is significantly impaired in the presence of ethionamide due to EthA-mediated conversion of this prodrug into an antimycobacterial nicotinamide adenine dinucleotide derivative. EthR-mediated repression of ethA transcription requires rather high clinical doses of ethionamide (up to 1 g/day, Holdiness, M. R., Clin Pharmacokinet 9, 511-44 (1984)) which is associated with severe side-effects including neurotoxicity and fatal hepatotoxicity, yet is often still insufficient to reach minimum inhibitory levels in the blood stream. Therefore, 2-phenylethyl butyrate-triggered dissociation of EthR from the ethA promoter resulting in derepression of ethA increases the sensitivity of *Mycobacterium* to ethionamide-based therapy. Growth of *M. bovis* BCG and *M. tuberculosis* H37Rv in the presence of sub-inhibitory ethionamide concentrations (0.25 and 0.5 μg/ml), which are easily reached by therapeutic doses, ($c_{max}$ (250 mg oral)=2 μg/ml, $t_{1/2}$=2 h) is dose-dependently inhibited by 0.5 and 2 mM 2-phenylethyl butyrate. Since 2-phenylethyl butyrate alone does not show any growth inhibitory effect it must act synergistically with ethionamide to kill the pathogen (FIG. 4).

Pharmaceutical Compositions

The invention relates to a pharmaceutical composition comprising a compound preventing EthR from binding to the ethA promoter and a thioamide or thiourea. In particular the invention relates to such a composition comprising a compound of formula 1 as defined hereinbefore, preferably selected from 4-phenyl-2-butanone, benzyl acetate, 3-phenylpropyl propionate and 2-phenylethyl butyrate, in particular 2-phenylethyl butyrate, and a compound of formula 2 as defined hereinbefore, preferably ethionamide.

As a consequence of adding a compound preventing EthR from binding to the ethA promoter to a pharmaceutical composition useful in the treatment of tuberculosis, the dose of the thioamide or thiourea, e.g. of ethionamide, may be substantially reduced, reducing thereby the known side effects without reducing its efficacy.

The pharmaceutical compositions of the invention are not only useful for the treatment of tuberculosis, i.e. a disease caused by *Mycobacterium tuberculosis*, but also for the treatment of diseases caused by related bacteria with EthR related proteins binding to the corresponding ethA related promoter, in particular *Mycobacterium leprae, Mycobacterium ulcerans, Mycobacterium marinum, Mycobacterium* sp. *MCS, Mycobacterium* sp. *KMS, Mycobacterium* sp. *JLS, Mycobacterium vanbaalenii, Mycobacterium avium* subsp. *paratuberculosis, Mycobacterium avium, Mycobacterium smegmatis, Mycobacterium gilvum, Mycobacterium abscessus, Acinetobacter baumannii, Renibacterium salmoninarum, Mycobacterium gilvum, Streptococcus pyogenes, Bacillus licheniformis, Clostridium spiroforme*, and *Bacillus anthracis*. Such diseases are leprosy, buruli-ulcer disease, atypical mycobacteriosis, Johne's and Crohn's disease, hot tub lung, lady Windermere syndrome, chronic lung disease, post-traumatic wound infections, post-tympanostomy tube otorrhea, disseminated cutaneous diseases, *Acinetobacter baumannii* caused infections, pharyngitis, impetigo, erysipelas, cellulitis, necrotizing fasciitis, scarlet fever, toxic shock septicaemia, peritonitis, ophthalmitis, diarrhoea and splenic fever.

Pharmaceutical compositions according to the invention are compositions for enteral administration, such as nasal, buccal, rectal or, especially, oral administration, and for parenteral administration, such as intravenous, intramuscular or subcutaneous administration. The compositions comprise the thioamide or thiourea, e.g. ethionamide, and the compound preventing EthR from binding to the ethA promoter alone or, preferably, together with a pharmaceutically acceptable carrier. The dosage of the active ingredients depends upon the patient, its age, weight, and individual condition, the individual pharmacokinetic data, and the mode of administration.

The invention relates also to pharmaceutical compositions for use in a method for the prophylactic or especially therapeutic management of the human or animal body, in particular in a method of treating tuberculosis, leprosy, buruli-ulcer disease, atypical mycobacteriosis, Johne's and Crohn's disease, hot tub lung, lady Windermere syndrome, chronic lung disease, post-traumatic wound infections, post-tympanostomy tube otorrhea, disseminated cutaneous diseases, *Acinetobacter baumannii* caused infections, pharyngitis, impetigo, erysipelas, cellulitis, necrotizing fasciitis, scarlet fever, toxic shock septicaemia, peritonitis, ophthalmitis, diarrhoea and splenic fever.

The invention relates also to processes and to the use of compounds preventing EthR from binding to the ethA promoter for the manufacture of pharmaceutical preparations which further comprise a thioamide or thiourea, e.g. ethionamide, as active component.

The pharmaceutical compositions comprise from approximately 5% to approximately 95% of a mixture of a thioamide or thiourea, e.g. of ethionamide, and of a compound preventing EthR from binding to the ethA promoter in relative molar amounts of between 1:1 up to 1:10,000, preferably 1:10 up to 1:5000. Single-dose administration forms comprise from approximately 20% to approximately 90% of the mentioned mixture, and forms that are not of single-dose type from approximately 5% to approximately 20% of the mentioned mixture. Unit dose forms are, for example, coated and uncoated tablets, ampoules, vials, suppositories, or capsules. Further dosage forms are, for example, ointments, creams, pastes, foams, tinctures, lip-sticks, drops, syrups, sprays, and the like. Examples are capsules containing from about 0.05 g to about 1.0 g of a mixture of the active ingredients.

It is also possible to use the mixture of a thioamide or thiourea, e.g. of ethionamide, and of a compound preventing EthR from binding to the ethA promoter in two separate pharmaceutical unit dose forms, and such a combination is also part of the present invention. For example, a thioamide or thiourea, e.g. ethionamide, may be used in amounts of 0.01 g to about 0.5 g, e.g. in commercially available dose forms comprising from 0.05 g to about 0.5 g ethionamide, in combination with a different or same dose form comprising the compound preventing EthR from binding to the ethA promoter, for example 2-phenylethyl butyrate, in amounts of 0.5 g to about 5.0 g, as a kit of parts.

The pharmaceutical compositions of the present invention are prepared in a manner known per se, for example by means of conventional mixing, granulating, coating, dissolving, emulsifying or lyophilizing processes. Optionally, the compound preventing EthR from binding to the ethA promoter, e.g. 2-phenylethyl butyrate, can be formulated in liposomes.

For parenteral administration solutions of the active ingredients are preferred, and also suspensions, emulsions or dispersions, especially isotonic aqueous solutions, dispersions, emulsions or suspensions which, for example in the case of lyophilized compositions comprising the active ingredients alone or together with a carrier, for example mannitol, can be made up before use. The pharmaceutical compositions may be sterilized and/or may comprise excipients, for example preservatives, stabilizers, wetting agents and/or emulsifiers, solubilizers, salts for regulating osmotic pressure and/or buffers and are prepared in a manner known per se, for example by means of conventional dissolving and lyophilizing processes. The said solutions or suspensions may comprise viscosity-increasing agents, typically sodium carboxymethylcellulose, carboxymethylcellulose, dextran, polyvinylpyrrolidone, or gelatins, or also solubilizers, e.g. Tween 80® (polyoxyethylene(20)sorbitan mono-oleate).

Suspensions in oil comprise as the oil component the vegetable, synthetic, or semi-synthetic oils customary for injection purposes. In respect of such, special mention may be made of liquid fatty acid esters that contain as the acid component a long-chained fatty acid having from 8 to 22, especially from 12 to 22, carbon atoms. The alcohol component of these fatty acid esters has a maximum of 6 carbon atoms and is a monovalent or polyvalent, for example a mono-, di- or trivalent, alcohol, especially glycol and glycerol. As mixtures of fatty acid esters, vegetable oils such as cottonseed oil, almond oil, olive oil, castor oil, sesame oil, soybean oil and groundnut oil are especially useful.

The manufacture of injectable preparations is usually carried out under sterile conditions, as is the filling, for example, into ampoules or vials, and the sealing of the containers.

Suitable carriers for oral compositions are especially fillers, such as sugars, for example lactose, saccharose, mannitol or sorbitol, cellulose preparations, and/or calcium phosphates, for example tricalcium phosphate or calcium hydrogen phosphate, and also binders, such as starches, for example corn, wheat, rice or potato starch, methylcellulose, hydroxypropyl methylcellulose, sodium carboxymethylcellulose, and/or polyvinylpyrrolidone, and/or, if desired, disintegrators, such as the above-mentioned starches, also carboxymethyl starch, crosslinked polyvinylpyrrolidone, alginic acid or a salt thereof, such as sodium alginate. Additional excipients are especially flow conditioners and lubricants, for example silicic acid, talc, stearic acid or salts thereof, such as magnesium or calcium stearate, and/or polyethylene glycol, or derivatives thereof.

Tablet cores can be provided with suitable, optionally enteric, coatings through the use of, inter alia, concentrated sugar solutions which may comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropyl-methylcellulose phthalate. Dyes or pigments may be added to the tablets or tablet coatings, for example for identification purposes or to indicate different doses of active ingredient.

Pharmaceutical compositions for oral administration also include hard capsules consisting of gelatin, and also soft, sealed capsules consisting of gelatin and a plasticizer, such as glycerol or sorbitol. The hard capsules may contain the active ingredient in the form of granules, for example in admixture with fillers, such as corn starch, binders, and/or glidants, such as talc or magnesium stearate, and optionally stabilizers. In soft capsules, the active ingredient is preferably dissolved, emulsified or suspended in suitable liquid excipients, such as fatty oils, paraffin oil or liquid polyethylene glycols or fatty acid esters of ethylene or propylene glycol, to which stabilizers and detergents, for example of the polyoxyethylene sorbitan fatty acid ester type, may also be added.

Pharmaceutical compositions suitable for rectal administration are, for example, suppositories that consist of a combination of the active ingredient and a suppository base. Suitable suppository bases are, for example, natural or synthetic triglycerides, paraffin hydrocarbons, polyethylene glycols or higher alkanols.

The present invention relates furthermore to a method for the treatment of tuberculosis and related diseases, which comprises administering a mixture of a thioamide or thiourea, e.g. ethionamide, and of a compound preventing EthR from binding to the ethA promoter, for example 2-phenylethyl butyrate, in a quantity effective against said disease, to a warm-blooded animal requiring such treatment. The mixture can be administered in the form of pharmaceutical compositions comprising the mixture, or also the components separately at the same time or at different times within the day, prophylactically or therapeutically, preferably in an amount effective against the tuberculosis or related disease, to a warm-blooded animal, for example a human, requiring such treatment. In the case of an individual having a bodyweight of about 70 kg the daily dose of the mixture administered is from approximately 0.01 g to approximately 50 g, preferably from approximately 0.05 g to approximately 10 g, of a mixture containing the components in relative amounts of between 1:1 and 1:10,000.

The present invention relates especially also to the use of a compound preventing EthR from binding to the ethA promoter, for example a compound of formula 1 as defined hereinbefore, such as 4-phenyl-2-butanone, benzyl acetate, 3-phenylpropyl propionate and 2-phenylethyl butyrate, in particular of 2-phenylethyl butyrate, as such or in the form of a pharmaceutical formulation with at least one pharmaceutically acceptable carrier for the therapeutic and also prophylactic management of tuberculosis in combination with a thioamide or thiourea, for example a compound of formula 2, such as ethionamide, administered either separately or in a fixed combination. The preferred dose quantity, composition, and preparation of pharmaceutical formulations which are to be used in each case are described above.

The following Examples serve to illustrate the invention without limiting the invention in its scope.

EXAMPLES

Vector Design.

pWW489 ($P_{sv40}$-ethR-vp16-pA) is constructed by PCR-mediated amplification of ethR from genomic *M. bovis* DNA using oligonucleotides OWW400 (5'-gcatccatatgaattccaccatg accacctccgcggcca-3') and OWW401 (5'-cgatcgcgcgcggctgtacgcggagcggttctcgccgtaaatgc-3') followed by restriction and ligation (EcoRI/BssHII) into pWW35 [Weber, W. et al., Nat Biotechnol 20, 901-7 (2002)]. pWW491 ($O_{ethR}$-$P_{hsp70min}$-SEAP-pA) is obtained by direct cloning of a synthetic $O_{ethR}$ sequence (5'-gacgtcgatccacgctatcaacgtaatgtcgaggccgtcaacga gatgtcgacactatcgacacgtagcctgcagg-3') (AatII/SbfI) into pMF172 [Weber, W. et al., supra]. pWW488 ($P_{T7}$-ethR-vp16-$his_6$) is constructed by PCR-mediated amplification of ethR-vp16 from pWW489 using oligonucleotides OWW400 and OWW60 (5'-gctctagagcaagcttttaatggt gatggtgatgatgcccaccgtactgtcaattccaag-3') followed by cloning (NdeI/HindIII) into pRSETmod [Weber, C. C. et al., Biotechnol Bioeng 89, 9-17 (2005)]. pWW856 ($P_{ethR}$-gfp-pA) is constructed in three steps: (i) gfp is PCR-amplified from pLEGFP-N1 (Clontech, Palo Alto, Calif., USA) using oligonucleotides OWW848 (5'-ggcttgaattcaaaggagatataccatggt gagcaagggcgag-3') and OWW849 (5'-ggctttctagacaaaaacccctcaagacccgtttagaggccccaa ggggttatgctagttacttgtacagctcgtccatgccg-3') and cloned (EcoRI/XbaI) into pWW56 [Weber W. et al., supra] (pWW854). (ii) A synthetic $O_{ethR}$ sequence is directly cloned (HindIII/l EcoRI) into pWW854 (pWW855). (iii) $P_{ethR}$-gfp is excised (BamHI/StuI) from pWW855 and ligated (BamHI/ScaI) into pACYC177 (NEB, Ipswich, Mass., USA) (pWW856). pWW862 ($P_{T7}$-ethR-$his_6$) is assembled by annealing oligonucleotides OWW479 (5'-cgcgcatcatcatcat catcattaagcggccgca-3') and OWW480 (5'-agcttgcggccgcttaatgatgatgatgatgatg-3') and cloning the double-stranded DNA BssHII/HindIII into pWW488. pWW871 (5'LTR-$\Psi^+$-ethR-vp16-$P_{PGK}$-$neo^R$-3'LTR) was designed by cloning ethR-vp16 of pWW489 (EcoRI/BamHI) into pMSCVneo (Clontech). pWW35 ($P_{SV40}$-E-vp16-pA), pWW37 (ETR-$P_{hCMVmin}$-seap-pA) and pWW313 ($P_{T7}$-E-$his_6$-pA) are described in Weber, C. C. et al., supra.

Cell Culture.

Human embryonic kidney cells (HEK-293, ATCC CRL-1573) are cultivated in Dulbecco's modified Eagle's medium (DMEM; Invitrogen, Carlsbad, Calif., USA) supplemented with 10% fetal calf serum (Pan Biotech GmbH, Aidenbach, Germany, cat. no. 3302, lot P231902) and 1% of a penicillin/streptomycin solution (Sigma, St. Louis, Mo., USA, cat. no. 4458). Cells are transfected using standard calcium phosphate procedures [Weber W. et al., supra] and retroviral particles are produced according to the manufacturer's protocol (Clontech). $_{EthR}$HEK, transgenic for constitutive EthR-VP16 expression, is constructed by transducing HEK-293 with pWW871-derived retroviral particles followed by selection in DMEM containing 200 μg/ml neomycin and single-cell cloning. Cotransfection of $_{EthR}$HEK with pWW491 and pPUR (Clontech), subsequent selection in 200 μg/ml neomycin, 1 μg/ml puromycin followed by single-cell cloning resulted in $_{EthR}$HEK-SEAP. SEAP production is quantified as described in Schlatter, S. et al., Gene 282, 19-31 (2002).

Chemicals.

Pentyl acetate, methylphenyl acetate, 2-phenylethyl acetate, 4-phenyl-2-butanone (all Fluka) and 2-phenylethyl butyrate (Sigma) are commercially obtained. Methyl hexanoate is obtained by reacting hexanoic acid with thionylchloride in methanol. Butyl propionate, 2-phenylethyl propionate, 2-phenylethyl isopentanoate and 3-phenylpropyl propionate are prepared by reacting the corresponding alcohol with the acid chloride in dichloromethane using triethylamine as a base. Hexadecyl octanoate and benzyl-acetate are synthesized from the bromide and the acid with $K_2CO_3$ as the base in dimethylformamide. All esters are purified either by column chromatography (silica, ethylacetate/hexane) or distillation. ClogP is determined using Chemdraw Ultra 10.0 (CambridgeSoft, Cambridge, Mass., USA). Erythromycin (Sigma, St. Louis, Mo., USA, cat. no. E5389) is used as a 1,000× stock solution of 5 mg/ml in ethanol. Ethionamide is purchased from Sigma (cat. no. E6005) and prepared as 200× stock solution in DMSO.

FACS Analysis.

*E. coli* BL21(DE3) (Invitrogen), transformed with pWW488 and pWW856 or pWW856 alone, are grown overnight in Luria Bertani (LB) media containing 100 μg/ml ampicillin and 30 μg/ml kanamycin (for pWW856-transformed cells only). Then, 150 of *E. coli* suspension ($OD_{600}$ 1.3) is added to 2 ml fresh LB media containing antibiotics and 1 mM IPTG where indicated. After growth for 5.5 h at 37° C., 500 μl of the suspension is transferred to a new tube and centrifuged for 3 min at 800× g. The pellet is washed twice with 1 ml PBS and resuspended in 2 ml PBS for FACS analysis (>10,000 cells/sample), which is performed on a Cytomics FC500 (Beckman Coulter, Fullerton, Calif.) with 405 nm used for excitation and 510 nm for emission. FACS gates are shown in Supplementary FIG. 2.

ELISA.

EthR-$his_6$ is produced as previously described for E-$his_6$ [Weber, C. C. et al., supra] with the exception that the biotinylated operator sequence ($O_{ethR}$) is incubated with a 100 μl streptavidin agarose bead suspension (Novagen, Madison, Wis., USA, cat. no. 69203) for 1 h at 4° C. while rotating.

In Vivo Methods.

$_{EthR}$HEK-SEAP is encapsulated in alginate-poly-L-lysine-alginate capsules (200 cells/capsule) as described previously [Weber W. et al., supra]. Mice are injected intraperitoneally with 700 μl capsule suspension containing $2\times10^6$ cells. One and 25 hours post capsule implantation, the mice are injected with 2-phenylethyl butyrate at the indicated concentration (the injection volume is adjusted to 100 μl by adding canola oil (Migros, Zurich, Switzerland)). 48 hours post capsule implantation, serum samples are analyzed for SEAP expression. Dissection of the animals reveals no inflammation at the injection site.

Mycobacteria Cultivation and Susceptibility Testing.

*M. tuberculosis* H37Rv (ATCC27294) and *M. bovis* BCG #1721, a streptomycin-resistant derivative of BCG Pasteur, carrying a non-restrictive rpsL mutation (K42R) [Sander, P. et al., Mol Microbiol 52, 1543-52 (2004)] are grown in Middlebrook 7H9 supplemented with oleic acid, albumin, dextrose, catalase (Difco) and Tween 80 (0.05%) until mid-log phase. Ten-fold serial dilutions (20 μl) are streaked on Middlebrook 7H10-OADC agar plates containing solvent (DMSO, 200-fold dilution), ethionamide (0.25-0.5 μg/ml) and 2-phenylethyl butyrate (0.5 or 2 mM) where indicated. Plates are incubated at 37° C. and growth is documented after 2 and 3 weeks.

The invention claimed is:

1. A pharmaceutical composition comprising:

a compound preventing EthR from binding to the ethA promoter which compound is selected from the group consisting of benzyl acetate, 3-phenylpropyl propionate and 2-phenylethyl butyrate, and ethionamide.

2. The pharmaceutical composition according to claim 1, wherein the compound preventing EthR from binding to the ethA promoter is 2-phenylethyl butyrate.

3. The pharmaceutical composition according to claim 1, wherein the relative molar amounts of ethionamide and the compound preventing EthR from binding to the ethA promoter is between 1:1 and 1:10,000.

4. The pharmaceutical composition according to claim 1, wherein the composition consists of two separate dose forms containing ethionamide and the compound preventing EthR from binding to the ethA promoter, respectively.

5. A method for the treatment of tuberculosis, which comprises administering the pharmaceutical composition according to claim 1 in a quantity effective against said disease, to a warm-blooded animal requiring such treatment.

* * * * *